United States Patent [19]

Atsuta et al.

[11] Patent Number: 5,745,165
[45] Date of Patent: Apr. 28, 1998

[54] VIDEO SCOPE CAMERA

[75] Inventors: Hiroshi Atsuta, Katano; Kiyoko Oshima, Shijounawate; Kazuo Matsuura, Machida, all of Japan

[73] Assignee: Matsushita Electric Industrial Co., Ltd., Japan

[21] Appl. No.: 657,180

[22] Filed: Jun. 3, 1996

[30] Foreign Application Priority Data

Jun. 8, 1995 [JP] Japan .................. 7-141533

[51] Int. Cl.⁶ ............................... H04N 7/18
[52] U.S. Cl. ............... 348/65; 348/66; 348/68; 359/425; 359/823
[58] Field of Search .................. 348/65, 66, 68, 348/77, 164, 704; 396/84; 600/167; 74/128

[56] References Cited

U.S. PATENT DOCUMENTS

| | | | |
|---|---|---|---|
| 4,199,785 | 4/1980 | McCullough et al. | 348/704 |
| 4,775,887 | 10/1988 | Tachi | 348/77 |
| 5,115,307 | 5/1992 | Cooper et al. | 348/66 |
| 5,523,782 | 6/1996 | Williams | 348/66 |
| 5,527,261 | 6/1996 | Monroe et al. | 600/109 |
| 5,528,432 | 6/1996 | Donahoo | 359/894 |
| 5,541,702 | 7/1996 | Suzuki et al. | 396/133 |

FOREIGN PATENT DOCUMENTS

| | | |
|---|---|---|
| 62-246347 | 10/1987 | Japan . |
| 4-176436 | 6/1992 | Japan . |
| 4-285525 | 10/1992 | Japan . |
| 6-319696 | 11/1994 | Japan . |

*Primary Examiner*—Howard W. Britton
*Assistant Examiner*—Frank Snow
*Attorney, Agent, or Firm*—Parkhurst & Wendel

[57] ABSTRACT

A compact and light-weight video scope camera offering easy magnification changing operations. A hollow insert portion continuous to a grip to be held by an operator is provided with an imaging system at the leading end. Operating an operation switch on the grip allows operational movement of a selection mechanism in the insert portion to cyclically or selectively select, from plural preset distance values, a distance between a lens and an image pickup device in the imaging system, corresponding to which distance, the lens or the image pickup device is moved relative to each other by an imaging system component of mechanism to set any one of predetermined magnification modes. This results a compact, light-weight video scope camera offering easy magnification changing operations. The invention is applicable to various video scope cameras for diagnosis and/or treatment in dentistry and orthopedics and also for industrial or educational use.

16 Claims, 6 Drawing Sheets

VIDEO SCOPE CAMERA

FIELD OF THE INVENTION

The present invention relates to a video scope camera incorporating an image pickup device such as CCD and, more particularly to a video scope camera capable of varying an imaging magnification which can be used by a dental or stomatological surgical doctor to photograph an affected part and face of a patient.

BACKGROUND OF THE INVENTION

Recently, video scope cameras employing CCD have been used in dentistry or stomatological surgery for diagnosis and/or treatment of an affected part in the oral cavity of a patient.

Unlike common video cameras, such video scope cameras find specific applications such as for observation of a local part. Many of these video cameras are of a stick-like or pistol-like shape including a grip.

Among these, a prior art apparatus relevant to the present invention comprises image transmitting means, such as an image fiber, for transmitting the image of a subject to an image pickup device positioned externally of the oral cavity, as disclosed in Japanese Unexamined Patent Publication No. 62-246347 (1987).

Another conventional apparatus includes an objective lens replacement unit for varying the imaging magnification, as disclosed in Japanese Unexamined Patent Publication No. 4-176436 (1992).

Yet another apparatus includes a mirror to be placed internally of the oral cavity, and an objective lens, an image pickup device and an operating ring to be positioned externally of the oral cavity for allowing the image pickup device to be continuously moved by turning the operating ring to vary the magnification.

DISCLOSURE OF THE INVENTION

Such a video scope camera for imaging a local part to observe an affected part is required to have variable imaging magnification modes corresponding to the size of a subject. Additionally, the camera is desired to provide a simple and quick operation for such a purpose and to have a reduced size and weight as an apparatus held by the hand of an operator such as a doctor.

Unfortunately, the prior art apparatuses have an image pickup device at a portion not to be inserted in the oral cavity of a patient, thus requiring image transmitting means such as an image fiber or a lens having a long optical path. Hence, the apparatus has a complicated structure with a large number of components. In addition, the imaging system extends to the grip to be held by hand, making it difficult to reduce the size and weight of the apparatus.

The known video scope cameras suffer a low efficiency in varying the imaging magnification because a lens corresponding to a desired magnification has to be selected for replacement or the operating ring has to be gradually turned to a desired magnification.

In view of the foregoing, it is an object of the present invention to provide a compact and light-weight video scope camera facilitating the operation for varying the imaging magnification.

According to one aspect of the present invention, there is provided a video scope camera comprising an imaging system including a lens and an image pickup device; a grip to be held by an operator; an operation switch provided on the grip; imaging system component moving means for moving the lens or the image pickup device by predetermined moving amounts through the operation of the operation switch thereby setting predetermined magnification modes; and operational movement selecting means for cyclically or selectively setting any one of the moving amounts of the movement of the lens or the image pickup device, whereby the operation of the operation switch allows any one of the plural magnification modes to be selected.

With this arrangement, the aforesaid moving amounts of the movement of the lens or the image pickup device are changed through the operation of the operation switch so as to select desired magnification modes stepwise which are preset. Thus, there is realized a video scope camera facilitating the operation for changing the magnification.

In another aspect of the present invention, a video scope camera comprises a hollow grip to be held by an operator and a hollow insert portion continuous to the grip, which insert portion accommodates therein an imaging system including a lens and an image pickup device and disposed in the vicinity of the leading end of the insert portion, operational movement selecting means for cyclically or selectively selecting a distance between the lens and the image pickup device from a plurality of preset distance values, and imaging system component moving means for moving the lens or the image pickup device relative to each other by a predetermined moving amount correspondingly to the distance thus selected by the operational movement selecting means thereby setting a predetermined magnification mode, and which grip is provided with an operation switch for selecting any one of the aforesaid preset values of the operational movement selecting means from the exterior of the grip.

With this arrangement, optical image transmitting means and the imaging system provided in the grip may be eliminated, thus resulting in a reduced size of the apparatus. Additionally, the operation of the operation switch allows the operational movement selecting means to be switched for a stepwise selection of desired magnification modes which are preset, and thus is realized a video scope camera offering easy magnification changing operations.

The foregoing and other objects, features and attendant advantages of the present invention will become readily apparent from the following detailed description.

DETAILED DESCRIPTION OF THE PREFERRED EMBODIMENTS

The present invention will now be described by way of embodiments thereof with reference to FIGS. 1 to 9.

Figure 1:
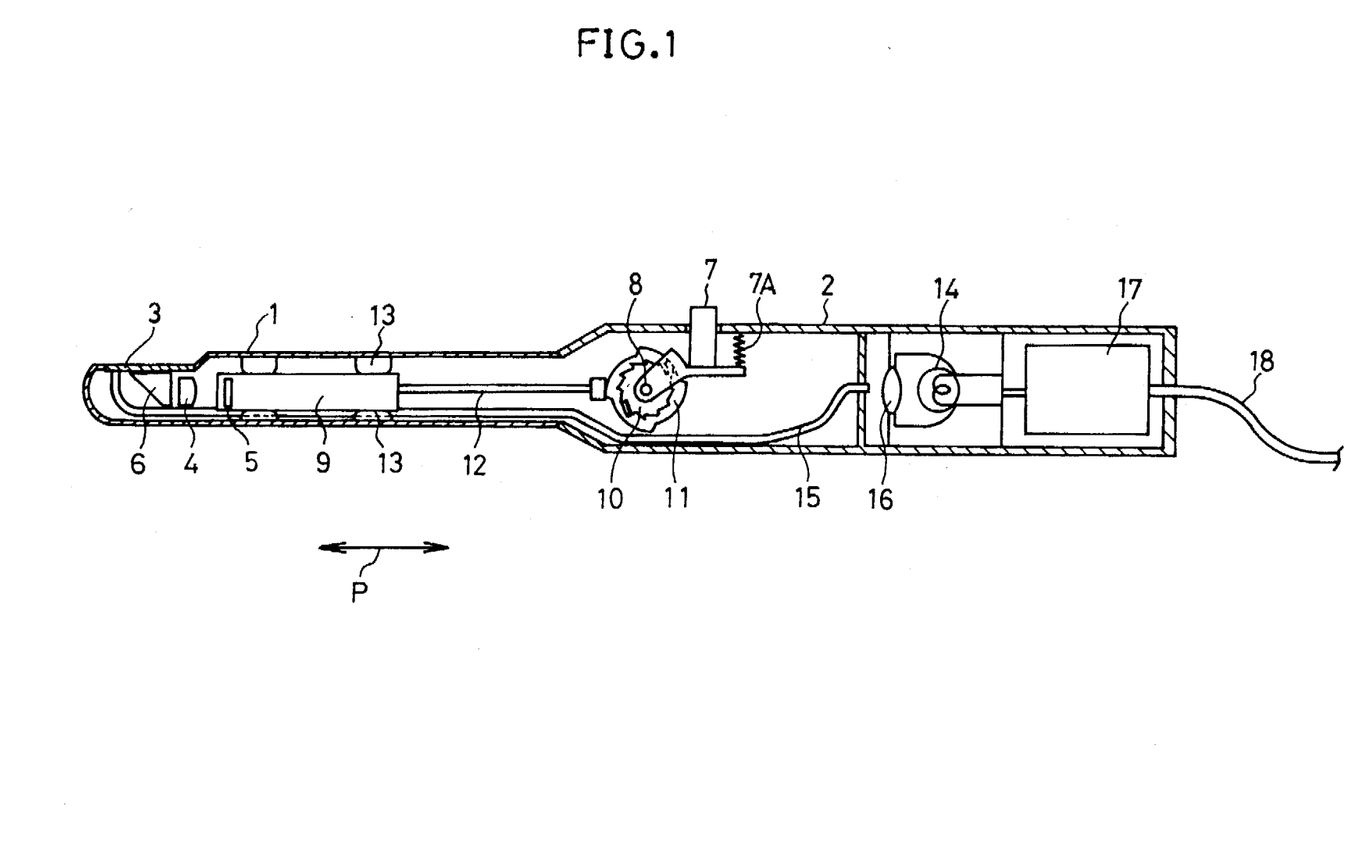
FIG. 1 is a sectional view showing a video scope camera according to an embodiment of the invention.

FIG.1 is a sectional view showing an intra oral video camera according to an embodiment of the invention. The video camera includes an insert portion 1 to be inserted into the oral cavity of a patient, a grip 2 to be held by a hand of an operator or a doctor, and a cover glass 3 of an entrance window on which image light reflected from a subject becomes incident. Provided in the vicinity of the leading end of the insert portion 1 is an imaging system comprising an objective lens 4, a CCD unit 5, and a prism mirror 6 for lateral vision. The objective lens 4 is comprised of a single lens having an aspheric surface for aberration correction.

It is noted that an iris diaphragm with a fixed aperture is provided between the objective lens 4 and the prism mirror 6, but is not shown in the figure. This embodiment is arranged such that the objective lens 4 is fixed while the CCD unit is movable.

The grip 2 is provided with a self-reset type pushbutton 7 adapted to reciprocate by means of a spring 7A, an operation cycling mechanism 8 (intermittent rotation mechanism) adapted to rotate 1/N of a full rotation in one direction in response to one depression of the pushbutton 7, and an image pickup device moving mechanism 9 for moving the CCD unit 5 along the optical path (direction indicated by an arrow P in the figure) as given a predetermined amount of displacement by the operation cycling mechanism 8.

The operation cycling mechanism 8 comprises a ratchet gear 10 and a rotary cam 11 as main components thereof and provides a stepwise change of displacement given to the image pickup device moving mechanism 9 in response to each depression of the pushbutton 7. By depressing the pushbutton 7 plural times (N times), the rotary cam 11 is rotated 360°, thereby causing the image pickup device moving mechanism 9 to resume its initial position.

The image pickup device moving mechanism 9 comprises a displacement transmission bar 12 and a guide 13 as main components thereof for converting a displacement caused by the rotary cam 11 into a movement of the CCD unit 5. The displacement transmission bar 12 is provided with a spring mechanism for urging the displacement transmission bar 12 rightwardly as viewed in the figure and a guide in order for the displacement transmission bar 12 to be constantly pressed against the rotary cam 11, which spring mechanism and spring are however not illustrated in the figure.

The grip 2 accommodates therein a light source 14 for illumination and a light guide 15 for guiding light received from the light source to the vicinity of the leading end of the insert portion 1 so as to allow the light to exit therefrom. If required, the light guide 15 may be provided with a converging lens 16 or a diverging lens at the light-incident side or the light-exit side thereof, respectively.

Reference character 17 denotes an electric circuit including an image pickup signal circuit and light source circuit which is provided within the grip 2, whereas reference character 18 denotes an electric cable for transmitting image pick up signals and supplying electric power. A camera control unit and a wiring within the main body, which are associated with the electric cable 18, are omitted in the figure.

With the construction as shown in FIG. 1, each time the operator depresses the pushbutton 7, the distance between the objective lens 4 and the CCD unit 5 varies so that the imaging magnification can be instantaneously varied. Depressing the pushbutton 7 N times causes the imaging magnification to resume its initial magnification.

The rotary cam 11 shown in FIG. 1 is of a shape resemblant to a square. Each side (¼) of the circumference of the rotary cam 11 is formed with a cam surface for changing the distance between the objective lens 4 and the CCD unit 5 correspondingly to three imaging magnification modes for imaging one tooth, entire mouth and whole face which are required of a video scope camera for use in dentistry. In this figure, N is set 12 (=3×4). By depressing the pushbutton 7, the magnification modes for tooth, mouth and face can be selectively switched. In this embodiment, the mode cycle is completed at every third depression of the pushbutton 7.

In the tooth mode, which is for the observation of an affected part, the purpose may be accomplished by setting the subject height (in the vertical direction of the screen) at approximately 1 cm; in the mouth mode, which is for the observation of a dentition or the like, the purpose may be accomplished by setting the subject height at approximately 10 cm; and in the face mode, which is for the observation of a dentition or for the acquisition of personal identification information of a patient, the purpose may be accomplished by setting the subject height at approximately 30 cm. The magnification ratio corresponding to the above three modes is about 30:3:1 which may be a most useful ratio as a magnification mode for use in a video scope camera for dentistry.

Thus with the construction of the invention, the magnification may be varied simply by depressing the pushbutton 7 serving as the operation switch. Hence, it is possible to realize an easier and faster magnification change than the conventional video scope cameras wherein the magnification is varied by changing the objective lens or by adjustment with the operating ring.

Further, the imaging system is disposed in the vicinity of the leading end of the insert portion 1 whereas the image pickup device moving mechanism 9 and the light source 14 are located rearwardly of the imaging system and, therefore, the means for transmitting an image to the grip 2 is not required. The elimination of the image transmission means advantageously enhances the sensitivity with a decreased light loss, thus contributing to a corresponding reduction in the required intensity of the illumination light, hence, of the light source. Additionally, the incorporation of the light source 14 within the main body eliminates the need for a separate light source unit and a light guide extending therefrom. This contributes to a further reduction in the required intensity of the light source correspondingly to the elimination of the long light guide which is conventionally employed. Thus, the invention provides for the downsizing and power saving of the apparatus.

The provision of the mechanisms including the image pickup device moving mechanism 9 and the operation cycling mechanism 8 utilizing the pressing force of the pushbutton 7 results in less power consumption as compared to a construction including an electric motor and a control circuit therefor. Such an arrangement may also facilitate reduction of the size and weight of the apparatus.

If the video scope camera is provided with a close-up mode for an affected part and a close-shot mode for face for the acquisition of personal identification information of a patient in order to be used for diagnosis and/or treatment not only in dentistry but also in other medical fields, the video camera will be effectively used for the preparation of electronic information for clinical chart to be stored in a computer as pictorial information.

The distance between a subject and the objective lens is set by selecting a focal length of the objective lens. For example, such a distance in the close-up mode is set less than about 10 cm and that in the close-shot mode is set from about 30 to about 100 cm. The subject height in the face mode is about 30 cm and the face can be focused by moving either the lens or the image pickup device in a direction so as to decrease the distance between the lens and the image pickup device relative to the close-up mode.

Another embodiment of the invention is illustrated in FIGS. 2 through 9.

Figure 2:
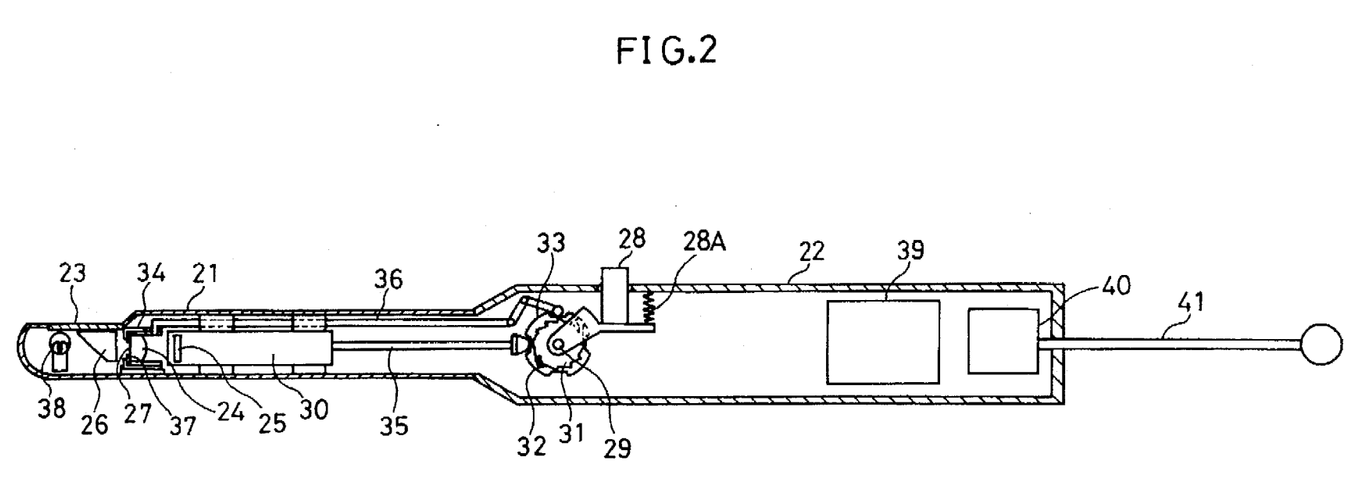
FIG. 2 is a sectional view showing a video scope camera according to another embodiment of the invention.

With reference to FIG. 2, an insert portion is indicated at 21, a grip at 22 and a cover glass of an entrance window at 23. Disposed in the vicinity of the leading end of the insert portion 21 is an imaging system including an objective lens 24, a CCD unit 25 and a prism mirror 26 for lateral vision.

An iris diaphragm 27 adapted to change the size of the aperture is provided between the objective lens 24 and the prism mirror 26. The grip 22 is provided with a self-reset type pushbutton 28 adapted to reciprocate by means of a spring 28A, an operation cycling mechanism 29 (intermittent rotation mechanism) adapted to rotate 1/N of a full rotation in one direction in response to one depression of the pushbutton 28, and an image pickup device moving mechanism 30 for moving the CCD unit 25 along the optical path as given by a predetermined amount of displacement by the operation cycling mechanism 29.

The operation cycling mechanism 29 comprises a ratchet gear 31 and first and second rotary cams 32 and 33 as main components thereof and provides a stepwise change of displacement given to the image pickup device moving mechanism 30 in response to each depression of the pushbutton 28. By depressing the pushbutton 29 N times, the first and second rotary cams 32 and 33 are rotated 360°.

Figure 3:
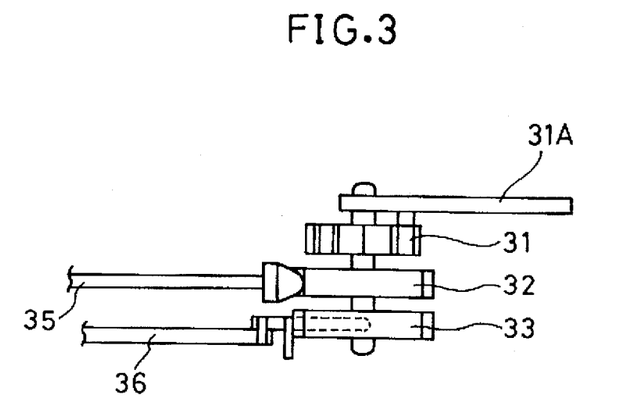
FIG. 3 is a diagram showing the construction of an operation cycling mechanism in the embodiment shown in FIG. 2.
Figure 4:
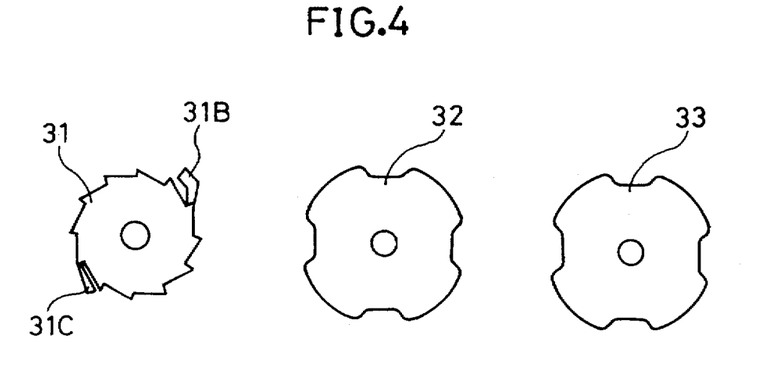
FIG. 4 is a schematic illustration of cams of the operation cycling mechanism in the embodiment shown in FIG. 2.

FIGS. 3 and 4 illustrate the operation cycling mechanism 29. FIG.3 is a side elevation thereof wherein a lever component for turning the ratchet gear 31 is indicated at 31A. FIG.4 illustrates the respective shapes of the ratchet gear 31 and first and second rotary cams 32 and 33. Indicated at 31B is a driving claw component provided at the lever component 31A whereas an anti-reverse claw component for the ratchet gear 31 is indicated at 31C. These may be practiced by a known ratchet gear mechanism and, therefore, the description thereof is omitted.

Referring back to FIG. 2, the first rotary cam 32 serves to give a displacement to the image pickup device moving mechanism 30. The second rotary cam 33 serves to give a displacement to an aperture size changing mechanism 34 for changing the size of the aperture of the iris diaphragm 27.

By depressing the pushbutton 28 N times, both the first and second rotary cams 32 and 33 are rotated 360°, so that the position of the CCD unit 25 and the size of the iris diaphragm 27 are changed stepwise synchronously.

The image pickup device moving mechanism 30 comprises a displacement transmission bar 35 as a main component thereof and has a similar arrangement and operation to the aforementioned embodiment. The displacement transmission bar 35 is provided with a spring mechanism and a guide for reset (not illustrated in the figure).

The aperture size changing mechanism 34 comprises a displacement transmission bar 36 and aperture blades 37 as main components thereof and is adapted to convert a displacement set by the second rotary cam 33 into a displacement of the aperture blades 37 thereby changing the size of the aperture. The displacement transmission bar 36 is provided with a spring mechanism and a guide for reset (not illustrated in the figure).

Figure 5:
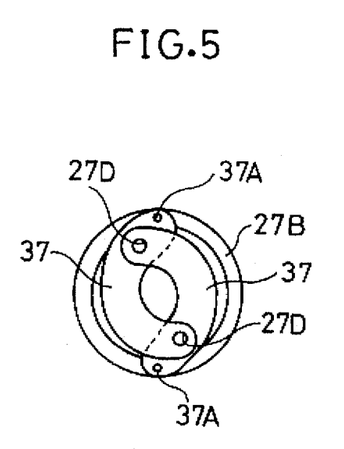
FIG. 5 is a schematic illustration of an iris diaphragm assuming a small aperture position in the above embodiment.
Figure 6:
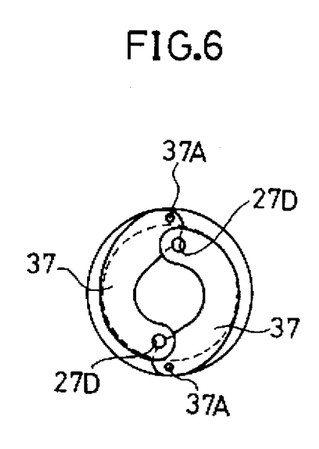
FIG. 6 is a schematic illustration of an iris diaphragm assuming a large aperture position in the embodiment shown in FIG. 2.
Figure 7:
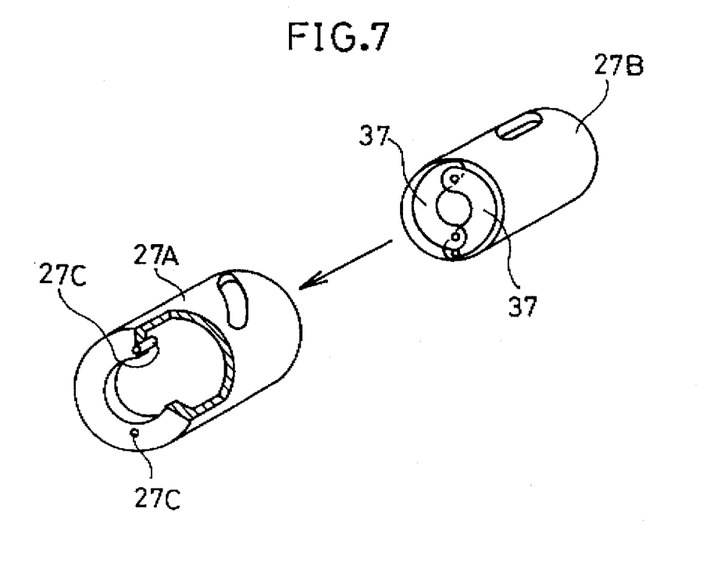
FIG. 7 is a partially cut away exploded view of the iris diaphragm in the embodiment shown in FIG. 2.

FIGS. 5 through 7 illustrate the iris diaphragm 27. FIGS. 5 and 6 illustrate the iris diaphragm 27 assuming a small aperture position and a large aperture position, respectively, by means of the aperture blades 37. FIG. 7 illustrates a turn ring 27A and a fixed ring 27B, which are components of the iris diaphragm 27.

As shown in FIG. 7, the iris diaphragm 27 has the fixed ring 27B inserted into the turn ring 27A, and pins 27C disposed interiorly of the turn ring 27A engage corresponding pin holes 27D of the aperture blades 37 disposed on the fixed ring 27B. The turn ring 27A is turned by the movement of the displacement transmission bar 36, which in turn causes the aperture blades 37 to pivot about respective fulcrums 37A whereby the size of the aperture is changed. Such an aperture blade mechanism can be implemented by the known art, and, therefore, the description thereof is omitted.

Now description will be given referring back to FIG. 2. A light source 38 is disposed in the vicinity of the leading end of the insert portion 21. The grip 22 accommodates therein a power source 39 such as a dry cell or a storage battery, and a transmitter 40 for transmitting an electric wave.

The power source 39 supplies electric power to the electric circuits of the CCD unit 25, light source 38, transmitter 40 and the like. The transmitter 40 converts imaging signal obtained by the CCD unit 25 into electric wave and transmits it to a receiver (not shown) placed at a separate location through a transmission antenna 41. The wiring within the grip 22 is not shown.

Figure 8:
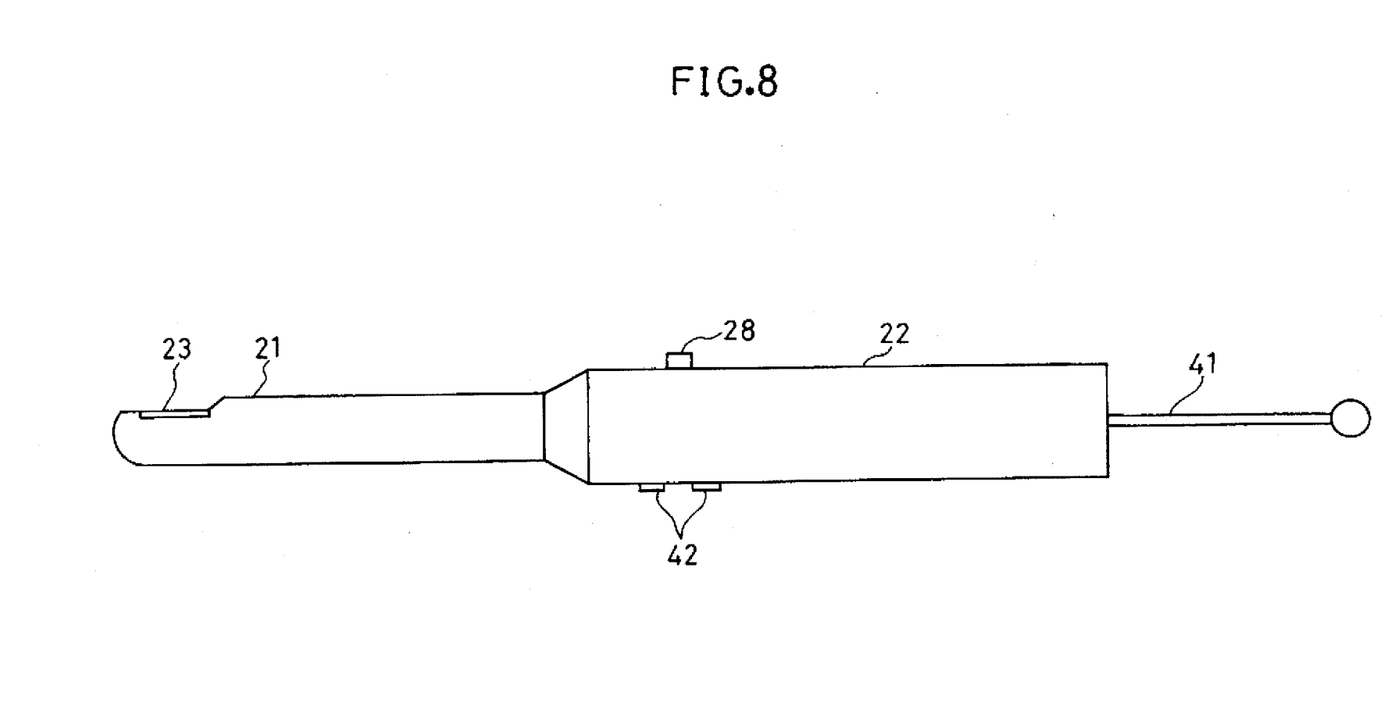
FIG. 8 is a schematic view showing the appearance of the video scope camera of the embodiment shown in FIG. 2.

FIG. 8 is a schematic view showing the appearance of the embodiment of FIG. 2 wherein an electric switch 42 is provided such that the circuit operations for imaging and signal transmission can be controlled from the exterior of the grip 22.

This allows for instantaneous changes in the imaging magnification and the aperture size at each depression of the pushbutton 28 by the operator. In this case, the operator may adjust the focus by varying the distance to a subject with the leading end of the insert portion 21 inserted into the depth of field.

It is generally difficult to adjust the focus in the close-up mode for imaging a tooth or the like since the imaging magnification is great while the depth of field is small. Accordingly, when the close-up mode is selected, the embodiment is adapted to secure a range for the adjustment of the focus by decreasing the size of the aperture to increase the depth of field. At this time, the insufficiency of the brightness due to the decreased size of the aperture is supplemented by illumination light from the light source 38.

In the close-shot mode, conversely, it is easier to secure the depth of field due to a smaller imaging magnification and, therefore, the brightness is obtained by increasing the size of the aperture. Such operations for the adjustment of the imaging magnification and the aperture size may be readily performed by merely depressing the single pushbutton 28.

More specifically, the operation of the pushbutton 28 is made operatively associated with the control circuit of the light source 38 so that the light source 38 is actuated only in the close-up mode for tooth while on the other hand the imaging in the close-shot mode for face utilizes only ambient light without actuation of the light source 38, whereby, power saving is achieved.

It should be noted that although the light source 38 is adapted to be turned ON/OFF cooperatively with the operation of the pushbutton 28 in this embodiment, an alternative arrangement is possible such that the brightness of the light source 38 is switched cooperatively with the operation of the pushbutton 28.

Thus, this embodiment is preferably used for the diagnostic and/or treatment purpose because light from the light source 38 is merely required to be turned off or lowered in the close-shot mode for face to prevent a patient from feeling glare on the eyes.

Figure 9:
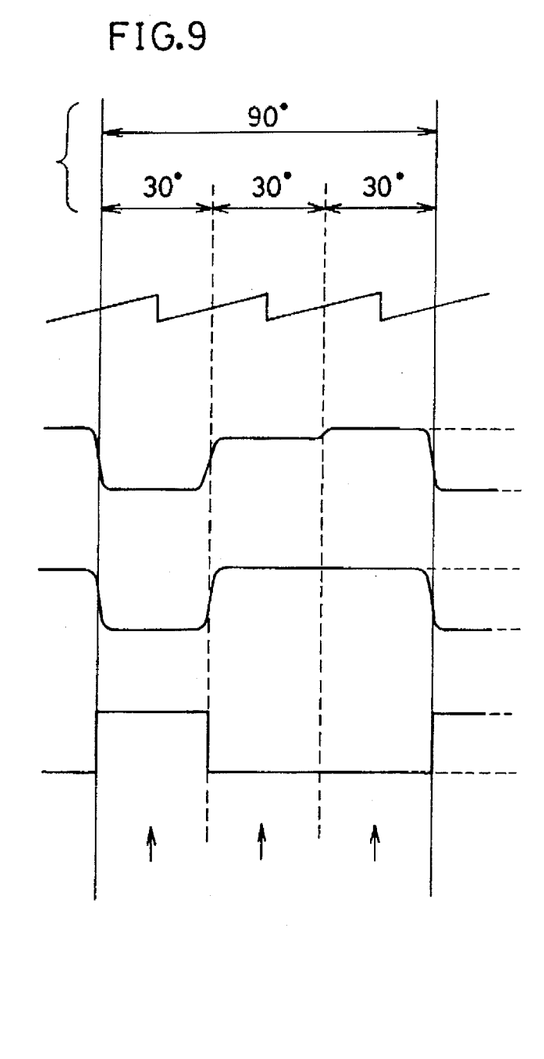
FIG. 9 is a timing chart of operations of the video scope camera of the present invention.

FIG. 9 is a timing chart of the operations of the embodiment.

In FIG. 9, the first and second rotary cams 32 and 33 achieve ¼ of a full rotation, or rotate 90° as indicated by the rotation angle (1). During this rotation, the cams are rotated on a 30° step basis by means of the ratchet gear indicated at (2) so as to switch the magnification mode (6) between tooth mode, mouth mode and face mode.

The chart (3) of the first rotary cam 32 represents the varying amount of displacement set by the first rotary cam 32. The variation in the amount of displacement causes the CCD unit 25 to move back and forth correspondingly to the respective magnification modes and to retreat to the rearmost position in the close-up mode.

The chart (4) of the second rotary cam 33 represents the varying amount of displacement set by the second rotary cam 33, which amount of displacement determines the size of the aperture. The iris diaphragm 27 is adapted to open wide in the magnification modes for mouth and face.

According to the chart (5) of the light source 39, light is turned on in the close-up mode with the aperture size decreased whereas light is turned off in the magnification modes for mouth and face with the aperture size increased. The operations of the present embodiment is performed according to the above timing.

As described above, the provision of the aperture size changing mechanism 34 synchronized with the image pickup device moving mechanism 30 allows the aperture size to be adjusted corresponding to the desired magnification mode while making it easy to secure the required depth of field and brightness. If the light source 38 is made operatively associated therewith, the video scope camera of the invention will become more convenient in use.

The elimination of the image transmission means and the light guide advantageously contributes to an increased sensitivity with a decreased light loss. Hence, the downsizing and power saving of the light source 38 can be readily achieved.

The grip 22 accommodates therein the power source 39 and the transmitter 40 instead of the light source system and the imaging system, and hence, a compact, cordless video scope camera is realized.

All of the illustrated embodiments of the invention employ the pushbutton in combination with the operation cycling mechanism serving as the operational movement selecting means for the imaging system components wherein the operation is cycled in one direction in the order of tooth, mouth, face, tooth, mouth, face, . . . . However, another mechanism may be employed. For example, a linear or a rotary slide switch adapted to be positioned at specific points may be used as the operation switch in combination with an operation cycling mechanism adapted for reciprocatory operations between tooth, mouth, face, tooth, mouth, face, . . .

Alternatively, there may be employed a toggle switch or a lever adapted for reciprocatory or rotary angle changing.

These mechanisms are advantageous in that the magnification mode can be confirmed from the position of the operation switch. Further, a plurality of operation switches may be employed for direct selection of any one of the magnification modes for tooth, mouth and face. A variety of known switches, operation selecting methods and cycling methods are applicable to the practice of the present invention.

The aforementioned embodiments employ the rotary cam for setting the amount of movement of the imaging system components. Alternatively, a variety of known mechanisms such as a slide switch, a toggle switch, a link mechanism for converting the amount of displacement of a lever and a gear mechanism may be used for setting the displacement.

There may be employed displacement transmission means such as those utilizing a wire or a belt, or pneumatic or hydraulic pressure. The present invention advantageously provides an easy arrangement of means for moving the imaging system components to the imaging portion because of the elimination of the optical image transmission system.

Instead of changing the magnification modes in complete mechanical fashion, another mode of the invention may be practiced such that a combination of an electric switch and known electric drive means such as a step motor, a piezoelectric element and an ultrasonic motor is employed for changing the modes. It is needless to note that instead of the CCD unit, the objective lens is caused to move. As described above, a variety of modes for practicing the invention are possible.

Additionally, in the embodiments of the invention it is also possible to electrically extract and enlarge CCD signals from a part of an imaged area thereby allowing the display magnification to be changed without moving the objective lens or the CCD unit.

Thus, the present invention makes it possible to provide a small-size, light-weight video scope camera offering easy magnification changing operations for use in applications of the type wherein the size of an imaging subject is previously restricted to some sizes. The present invention is applicable to a variety of video scope cameras for diagnosis and/or treatment in dentistry and orthopedics as well as for industrial and educational use, thus providing a high industrial merit.

While the presently preferred embodiments of the present invention have been described in detail, as will be apparent with those familiar with the art, certain changes and modifications can be made in embodiments without departing from the spirit and scope of the present invention as defined in the following claims.

What is claimed is:

1. A video scope camera comprising:
    an imaging system including a lens and an image pickup device provided in a casing comprising an insert portion;
    a grip to be held by an operator;
    a mechanical operation switch provided on said grip;
    imaging system component moving means for moving said lens or said image pickup device with respect to the insert portion by predetermined discrete degrees of displacement by direct operation of said mechanical operation switch, thereby defining a plurality of predetermined magnification modes; and
    operational movement selecting means for selecting one of the discrete degrees of displacement of said lens or said image pickup device, thereby selecting one of the magnification modes.

2. A video scope camera as set forth in claim 1, wherein said imaging system component moving means comprises an image pickup device moving mechanism for displacing the position of said image pickup device in response to a depression of said operation switch disposed on said grip located rearwardly of the imaging system thereby setting a magnification mode; and wherein said operational movement selecting means comprises an operation cycling mechanism for cyclically setting any one of the discrete distance values.

3. A video scope camera as set forth in claim 1, wherein said imaging system includes an iris diaphragm, and the video scope camera further includes aperture size changing means for changing the size of the iris diaphragm cooperatively with the imaging system component moving means.

4. A video scope camera as set forth in claim 3, wherein the plural magnification modes include at least a close-up mode for imaging an affected part of a patient and a close-shot mode for imaging the whole face of a patient.

5. A video scope camera as set forth in claim 4, further including a light source and light source control means, operatively associated with said imaging system component moving means, for illuminating the light source while decreasing the size of the aperture of said iris diaphragm in said close-up mode and for lowering or turning off the light source while increasing the size of the aperture of said iris diaphragm in said close-shot mode.

6. A video scope camera as set forth in claim 1, wherein the predetermined magnification modes include a high magnification mode for imaging one tooth of a patient, an intermediate magnification mode for imaging the entire mouth of a patient, and a low magnification mode for imaging the whole face of a patient.

7. A video scope camera as set forth in claim 6, wherein the ratio of the three magnification modes is set at approximately 30:3:1.

8. A video scope camera as set forth in claim 1, wherein said insert portion has an entrance window on which imaging light becomes incident, said insert portion being adapted to be inserted into an oral cavity, and said imaging system is disposed in the vicinity of the leading end of said insert portion, said imaging system including a light source.

9. A video camera as set forth in claim 1, further including:

a grip from which said insert portion extends, said grip housing therein an illumination light source, said insert portion having at the leading end thereof an entrance window on which imaging light becomes incident, said imaging system being positioned in the vicinity of the leading end of the insert portion; and optical guide means for guiding light from the light source toward said imaging system in the insert portion.

10. A video scope camera as set forth in claim 1, wherein said imaging system component moving means is adapted to displace said image pickup device with respect to the insert portion.

11. A video scope camera as set forth in claim 1, wherein the predetermined discrete degrees of displacement are cyclically settable.

12. A video scope camera comprising:

a hollow grip to be held by an operator and a hollow insert portion extending from said grip, an imaging system including a lens and an image pickup device and being disposed in the insert portion in the vicinity of the leading end of said insert portion, operational movement selecting means for selecting a distance between said lens and said image pickup device from a plurality of preset discrete distance values, and imaging system component moving means for moving one of said lens and said image pickup device relative to the other and relative to the insert portion by a predetermined discrete degree of displacement corresponding to the distance selected by said operational movement selecting means, thereby setting a predetermined magnification mode, wherein said grip includes a mechanical switch for directly actuating said operational movement selecting means from the exterior of said grip.

13. A video scope camera as set forth in claim 12, wherein said imaging system component moving means is adapted to displace said image pickup device with respect to the insert portion.

14. A video scope camera as set forth in claim 12, wherein the predetermined discrete degrees of displacement are cyclically settable.

15. A video scope camera comprising:

a grip to be held by an operator; and an insert portion extending from the grip, said insert portion having an entrance window on which imaging light becomes incident and being adapted to be inserted into an oral cavity, one of said grip and said insert portion housing a light source, said insert portion accommodating in the vicinity of the leading end thereof an imaging system having a lens and an image pickup device, and said grip accommodating therein a transmitter for transmitting image signals fed from said imaging system, and a power source for commonly operating said image pickup device, said light source and said transmitter.

16. A video scope camera comprising:

an imaging system including a lens and an image pickup device provided in a casing comprising an insert portion;

a grip to be held by an operator;

an operation switch provided on said grip; and an imaging signal processing circuit for providing a plurality of discrete magnification modes of the video scope camera by extracting and enlarging image signals from the image pickup device, said imaging signal processing circuit being actuated directly by said operation switch.

* * * * *